United States Patent
Davis et al.

(10) Patent No.: US 6,436,711 B1
(45) Date of Patent: Aug. 20, 2002

(54) FLUOROMETRIC CONTROL OF AROMATIC OXYGEN SCAVENGERS IN A BOILER SYSTEM

(75) Inventors: Barbara H. Davis, Geneva; Linda M. Link, Carol Stream; John E. Hoots, St. Charles, all of IL (US)

(73) Assignee: Nalco Chemical Company, Naperville, IL (US)

( * ) Notice: Subject to any disclaimer, the term of this patent is extended or adjusted under 35 U.S.C. 154(b) by 112 days.

(21) Appl. No.: 09/737,261

(22) Filed: Dec. 13, 2000

(51) Int. Cl.[7] .............................................. G01N 35/08
(52) U.S. Cl. ........................................ 436/55; 436/172
(58) Field of Search .............................. 436/55, 34, 38, 436/52, 172; 210/745; 700/202, 266; 422/15, 16, 3

(56) References Cited

U.S. PATENT DOCUMENTS

| 4,929,364 | A |   | 5/1990  | Reardon et al. |         |
|-----------|---|---|---------|----------------|---------|
| 4,968,438 | A |   | 11/1990 | Soderquist et al. |      |
| 5,041,386 | A |   | 8/1991  | Pierce et al.  |         |
| 5,167,835 | A | * | 12/1992 | Harder ....................... | 210/750 |
| 5,278,074 | A |   | 1/1994  | Rao et al.     |         |
| 5,435,969 | A |   | 7/1995  | Hoots et al.   |         |
| 5,904,857 | A |   | 5/1999  | Bailey         |         |
| 6,315,909 | B1 | * | 11/2001 | Hoots et al. ................. | 210/745 |
| 6,336,058 | B1 | * | 1/2002  | Fowee ......................... | 700/266 |
| 6,346,200 | B1 | * | 2/2002  | Rooney ....................... | 210/757 |

* cited by examiner

Primary Examiner—Jill Warden
Assistant Examiner—Sam Siefk
(74) Attorney, Agent, or Firm—Margaret M. Brumm; Thomas M. Breininger

(57) ABSTRACT

A method of automatically controlling the addition rate of Fresh Oxygen Scavenger Product and Ultimate Oxygen Scavenger Product to a Boiler System is described and claimed. The method is based on the inherent fluorometric properties of certain Fresh Oxygen Scavenger Products and certain Ultimate Oxygen Scavengers in their reduced (unreacted) form and also, for the Ultimate Oxygen Scavengers, in their oxidized (reacted) form. It has also been found possible to enhance the fluorescent signal of certain Oxygen Scavengers by adding a borate buffer to the sample stream. By using the method of the instant claimed invention it is now possible to improve the overall control of Boiler Systems using certain Fresh Oxygen Scavenger Products and certain Ultimate Oxygen Scavenger Products.

4 Claims, 7 Drawing Sheets

Fluorescence of Gallic Acid measured at 300 nm excitation, 370 nm emission on Hitachi F4500 slits (ex/em): 5.0 nm/5.0 nm, PMT: 700 V

FLUOROMETRIC CONTROL OF AROMATIC OXYGEN SCAVENGERS IN A BOILER SYSTEM

FIELD OF THE INVENTION

This invention is in the field of boilers. Specifically it is in the field of control of oxygen scavenger being added to boilers. The control method is based on using fluorometric analytical tools.

BACKGROUND OF THE INVENTION

It is known that oxygen in aqueous environments in contact with carbon steel results in localized or pitting type corrosion, which can lead to tube failures. Dissolved oxygen in boiler feedwater needs to be low in order to reduce corrosion of the boiler feedwater lines and boiler internals. Make-up water to any boiler circuit is usually saturated with dissolved oxygen. In order to reduce the amount of dissolved oxygen present from the parts per million (hereinafter "ppm") level to the desired parts per billion (hereinafter "ppb") level, a known piece of equipment, referred to as a deaerator, is installed to remove the dissolved oxygen mechanically.

The remaining oxygen is removed by contacting the boiler make-up water with a chemical scavenger. An additional reason for adding a chemical scavenger is to provide insurance that the oxygen scavenging ability will also be available should there be unwanted leaked oxygen entering the boiler feedwater. The chemical scavenging of trace levels of oxygen from boiler feedwater is done by feeding a sacrificial material, which is readily oxidized in the boiler environment. This sacrificial material is typically referred to as a "boiler oxygen scavenger", or "oxygen scavenger" for short.

There are many known oxygen scavengers for use in boiler systems. By definition, an oxygen scavenger must be capable of being oxidized. Chemically speaking, oxygen scavengers can be inorganic or organic, and if organic, they can be aromatic or aliphatic. One subset of known oxygen scavengers are the aromatic oxygen scavengers.

Gallic Acid is a known aromatic oxygen scavenger. See U.S. Pat. No. 4,968,438, assigned to Nalco Chemical Company, which is incorporated by reference in its entirety. Claim 1 of this patent is:

"An improved method for scavenging dissolved oxygen from waters used to generate steam having a temperature of at least 185° F. which comprises treating said waters with at least 0.3 mole of Gallic acid per mole of oxygen contained in said boiler waters."

Also see U.S. Pat. No. 4,929,364, assigned to Nalco Chemical Company, which is incorporated by reference herein, in its entirety. Claim 3 of the '364 patent claims:

"A method for scavenging dissolved oxygen from waters used to generate steam which comprises treating said waters with at least 0.3 mole of Gallic Acid per mole of oxygen contained in said boiler water using an aqueous concentrate containing at least 1.15 weight percent Gallic Acid, said aqueous concentrate having a pH of at least 8.5, said pH having been adjusted by a water-soluble neutralizing amine of the type used to treat boiler waters, said neutralizing amine being present in sufficient amount to solubilize said Gallic Acid in said waters used to generate steam."

Control of boilers and other steam generating equipment is described and claimed in U.S. Pat. No. 5,041,386, assigned to Nalco, which is herein incorporated by reference, in its entirety. In the '386 patent, concentration cycles, percent life holding time for a component in the boiler and continuous treatment concentrations are monitored or determined in a Boiler System by adding to the feedwater an inert tracer in a predetermined concentration, $C_I$, which reaches a final concentration, $C_F$, at steady state in the boiler and which exhibits a blowdown concentration, $C_t$, at different points in time. The component is an inert tracer having no significant carryover in the steam, nor significant degradation during boiler cycles. The tracer is monitored by continuously converting a characteristic of its concentration to an analog that may be recorded as a function of time.

It would be desirable to have methods to ensure an optimal amount of aromatic oxygen scavenger is present in a boiler.

SUMMARY OF THE INVENTION

Figure 1:
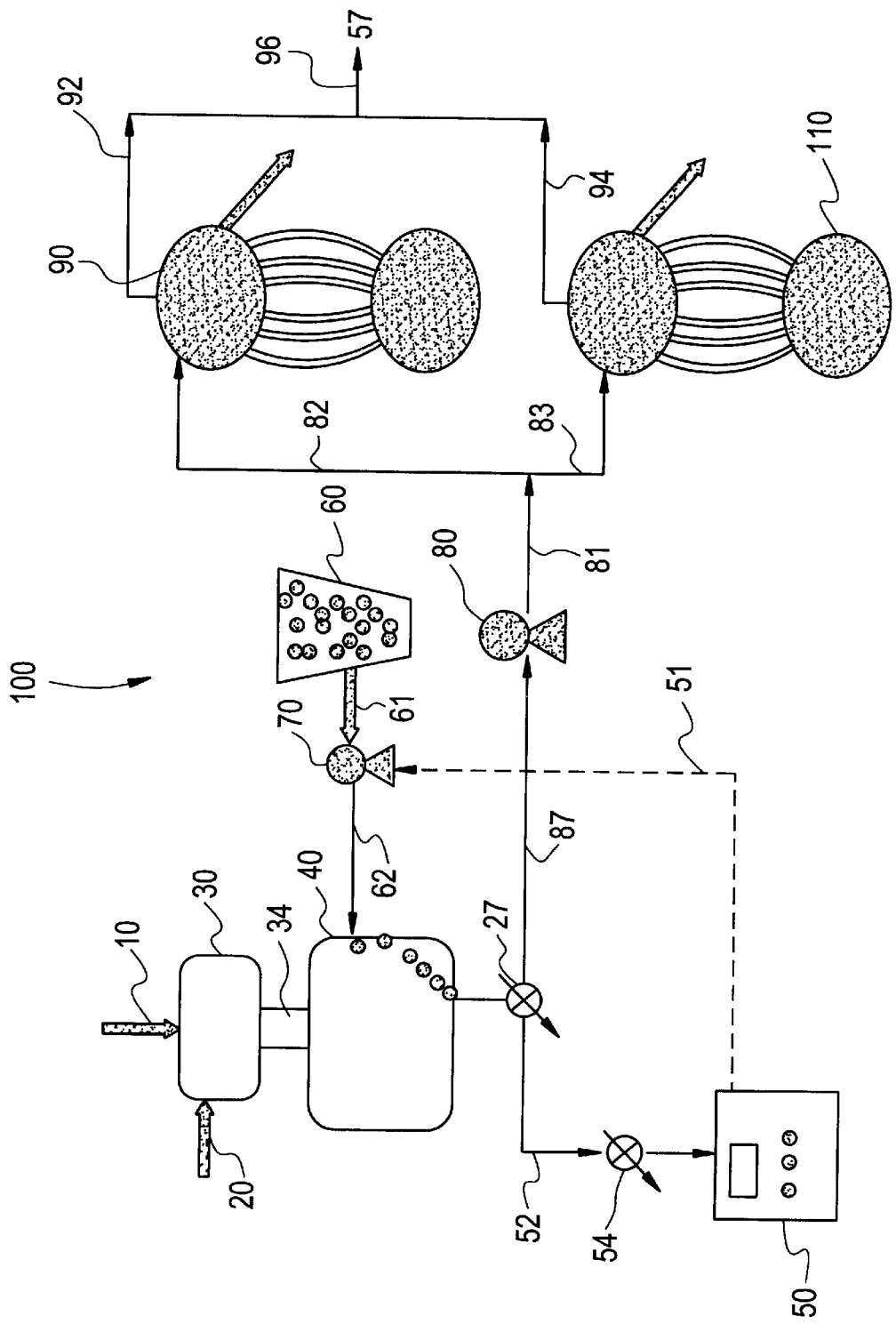
FIG. 1 illustrates a Boiler System with Gallic Acid being monitored fluorometrically with the signal from the fluorometer being used to control the feed rate of Fresh Oxygen Scavenger Product to the Boiler System.

The first aspect of the instant claimed invention is a method to control the addition of Fresh Oxygen Scavenger Product to a Boiler System comprising:

a) providing a Boiler System;

b) providing one fluorometer;

c) using said one fluorometer to detect the fluorescent signal of residual Oxygen Scavenger present in the boiler feedwater;

d) converting the fluorescent signal of said residual Oxygen Scavenger to the amount of said residual Oxygen Scavenger present in the boiler feedwater; and e) controlling the amount of Fresh Oxygen Scavenger Product being added to said Boiler System based on the amount of residual Oxygen Scavenger fluorometrically detected in said boiler feedwater.

The second aspect of the instant claimed invention is a method of enhancing the fluorescent signal of a fluorescent oxygen scavenger compound comprising:

a) providing a stream comprising a fluorescent oxygen scavenger compound selected from the group consisting of compounds with two or three adjacent hydroxyl groups on an aromatic ring;

b) providing one fluorometer;

c) adding borate to said stream; and d) using said fluorometer to detect the fluorescent signal of said fluorescent oxygen scavenger in said stream.

The third aspect of the instant claimed invention is a method to control the addition of Fresh Ultimate Oxygen Scavenger Product to a Boiler System comprising:

a) providing a Boiler System;

b) providing two fluorometers and a controller;

c) using the first of said two fluorometers to detect the fluorescent signal of residual Ultimate Oxygen Scavenger in the boiler feedwater;

d) using the second of said two fluorometers to detect the fluorescent signal of oxidized Ultimate Oxygen Scavenger in the boiler feedwater;

e) calculating a ratio of said residual Ultimate Oxygen Scavenger to said oxidized Ultimate Oxygen Scavenger in the boiler feedwater; and f) using said controller to control the amount of Fresh Ultimate Oxygen Scavenger Product added to said Boiler System based on comparing the calculated ratio of said residual Ultimate Oxygen Scavenger to said oxidized Ultimate Oxygen Scavenger in said boiler feedwater to an optimal setpoint ratio of said residual Ultimate Oxygen Scavenger to said oxidized Ultimate Oxygen Scavenger in said boiler feedwater.

DETAILED DESCRIPTION OF THE INVENTION

Aldrich refers to Aldrich Chemical Company, P.O. Box 2060, Milwaukee, Wis., USA 53201, telephone numbers (414) 273-3850 or (800) 558-9160.

Andover refers to Andover Corporation, 4 Commercial Dr., Salem, N.H., USA 03078-2800, telephone number (888) 893-9992.

For purposes of this patent application, an "aromatic ring" is any compound with one or two or three aromatic rings. For two or more rings the rings are fused. Suitable aromatic rings includes benzene, naphthalene, anthracene, phenanthrene and phenalene.

Borate refers to sodium tetraborate, $Na_2B_4O_7$. The Chemical Abstracts Service Registry Number for sodium tetraborate is 1330-43-4. Sodium tetraborate, 99%, is available from Aldrich, catalog number 22,173-2. Throughout this patent application the term borate is meant to include sodium tetraborate and also meant to include known hydrates of sodium tetraborate and mixtures thereof.

Gallic Acid refers to 3,4,5-trihydroxybenzoic acid. The CAS Registry Number for Gallic Acid is 149-91-7. Gallic Acid is available from Aldrich as the monohydrate, catalog number 39,822-5. Products containing Gallic Acid and base are available from Nalco. Throughout this patent application the term Gallic Acid is meant to include Gallic Acid and also meant to include known hydrates and salts of Gallic Acid and mixtures thereof.

Hydroquinone refers to p-dihydroxybenzene. It is also known as quinol or hydroquinol. The CAS Registry Number for Hydroquinone is 123-31-9. Hydroquinone is available from Aldrich in a 99% solution, catalog number H1,790-2. Throughout this patent application the term Hydroquinone is meant to include Hydroquinone and also meant to include known hydrates and salts of Hydroquinone and mixtures thereof.

LMI refers to Liquid Metronics Incorporated, a supplier of pumps.

Nalco refers to Nalco Chemical Company, One Nalco Center, Naperville, Ill., USA 60563, (630) 305-1000.

Propyl Gallate refers to Propyl 3,4,5-trihydroxybenzoate, which is also known as Benzoic Acid, 3,4,5-trihydroxy-, propyl ester. The Chemical Abstracts Service Registry Number for the inverted form of propyl gallate is 121-79-9.

3,4-dihydroxybenzhydrazide is also known as 3,4-dihydroxybenzoic acid hydrazide. The Chemical Abstracts Service Registry Number is 39635-11-5.

2-hydroxybenzhydrazide is also known as 2-hydroxybenzoic acid hydrazide. The Chemical Abstracts Service Registry Number is 936-02-7.

4-hydroxybenzhydrazide is also known as 4-hydroxybenzoic acid hydrazide. The Chemical Abstracts Service Registry Number is 5351-23-5.

Salicylal carbohydrazone is also known as carbonic dihydrazide, [(2-hydroxyphenyl)methylene]- or mono(salicylidene)carbohydrazone. The Chemical Abstracts Service Registry Number is 99223-49-1.

The first aspect of the instant claimed invention is a method to control the addition of Fresh Oxygen Scavenger Product to a Boiler System comprising:

a) providing a Boiler System;

b) providing one fluorometer;

c) using said one fluorometer to detect the fluorescent signal of residual Oxygen Scavenger present in the boiler feedwater;

d) converting the fluorescent signal of said residual Oxygen Scavenger to the amount of said residual Oxygen Scavenger present in the boiler feedwater; and e) controlling the amount of Fresh Oxygen Scavenger Product being added to said Boiler System based on the amount of residual Oxygen Scavenger fluorometrically detected in said boiler feedwater.

In the first aspect of the method of the instant claimed invention, residual Oxygen Scavenger is monitored and the addition of Fresh Oxygen Scavenger Product is controlled in the boiler feedwater based on the amount of fluorescent signal of residual Oxygen Scavenger detected. The characteristic fluorescent signal of Oxygen Scavenger changes as a function of its oxidation state, with the fluorescent signal of the residual (unreacted) Oxygen Scavenger being detectable. Some Oxygen Scavengers also have a detectable fluorescent signal in their oxidized (reacted) state. Unreacted Oxygen Scavenger is also referred to as Oxygen Scavenger in its reduced state. Reacted Oxygen Scavenger is also referred to as Oxygen Scavenger in its oxidized state.

Oxygen Scavenger that has different detectable fluorescent signals in both its unreacted and its reacted state is herein referred to as Ultimate Oxygen Scavenger.

"Residual Oxygen Scavenger" or "Oxygen Scavenger residual" are defined as the concentration of the reduced or active form of Oxygen Scavenger present in the boiler feedwater after the boiler feedwater has been put through a deaerator.

"Reacted Oxygen Scavenger" or "oxidized Oxygen Scavenger" or "Oxygen Scavenger in its oxidized state" are defined as the concentration of the oxidized Oxygen Scavenger present in the boiler feedwater after the boiler feedwater has been put through a deaerator. It is only possible to measure this oxidized Oxygen Scavenger fluorometrically when the Oxygen Scavenger is an Ultimate Oxygen Scavenger, which is an Oxygen Scavenger with a fluorescent signal in its residual (unreacted) state that is separate and distinguishable from the fluorescent signal of the oxidized (reacted) Oxygen Scavenger.

Oxygen Scavengers suitable for use in the first aspect of the method of the instant claimed invention include aromatic oxygen scavengers that are selected from the group consisting of Gallic Acid, Hydroquinone, Propyl gallate, 3,4-dihydroxybenzhydrazide, 2-hydroxybenzhydrazide, 4-hydroxybenzhydrazide and salicylal carbohydrazone. Of those Oxygen Scavengers that are suitable, the preferred Oxygen Scavengers are Gallic Acid and Hydroquinone. The most preferred Oxygen Scavenger is Gallic Acid.

FIG. 1 shows a first Boiler System 100 which includes first boiler 110, second boiler 90, make-up water 10, inlet steam 20, Fresh Oxygen Scavenger Product 60, deaerator storage section 40 and fluorometer 50. In operating this Boiler System, make-up water 10 and inlet steam 20 are combined in deaerator dome 30 until the appropriate temperature is reached. Output from deaerator dome 30 is sent to deaerator storage section 40 through the deaerator drop leg 34.

Fresh Oxygen Scavenger Product 60, can be Oxygen Scavenger by itself, or Oxygen Scavenger in a product formulation. For most preferred Oxygen Scavenger, Gallic Acid, two suitable product formulations, with all percentages being given in weight percent, are:

| Gallic Acid Product 1 | |
|---|---|
| Deionized water | 89.93% |
| 50% NaOH | 4.54% |
| Gallic Acid monohydrate | 5.53% |
| And | |
| Gallic Acid Product 2 | |
| Deionized water | 87.82% |
| Diethylaminoethanol | 6.65% |
| Gallic Acid monohydrate | 5.53% |

Both of these Gallic Acid Products are available from Nalco.

People of ordinary skill in the art of oxygen scavengers know the usual dose of Fresh Oxygen Scavenger Product to use in Boiler Systems. For instance, typically, Gallic Acid is capable of scavenging at dosages as low as 0.3 mole per one mole of oxygen present in the system.

Fresh Oxygen Scavenger Product 60 is pumped through transfer line 61 through Fresh Oxygen Scavenger Product Feedpump 70. Fresh Oxygen Scavenger Product Feedpump 70 pumps Fresh Oxygen Scavenger Product 60 through entry line 62 into the side of deaerator storage section 40 through coupling device 41 (not shown).

Fresh Oxygen Scavenger Product 60 reacts with dissolved oxygen to form oxidized Oxygen Scavenger. When the Oxygen Scavenger is Gallic Acid, the oxidized Oxygen Scavenger is chemically identified as 5-hydroxy, 3,4-dioxo, 1,5-cyclohexanediene-1-carboxylic acid, Chemical Abstracts Service Registry Number 65271-60-5. When the Oxygen Scavenger is Hydroquinone, the oxidized Oxygen Scavenger is benzoquinone ($C_6H_4O_2$, Chemical Abstracts Service Registry Number 106-51-4).

Boiler feedwater exits deaerator storage section 40 and travels through boiler feed line 87 until it reaches boiler feedpump 80. Boiler feedpump 80 operates anywhere from 10 psig (the minimum head pressure to feed the pump) to about 180 psig. At pressures above 150 psig, Boiler feedpump 80 is considered a high pressure boiler feedpump. Boiler feedpump exit line 81 conveys high pressure water at about 104° C. through first boiler feed line 83 which enters first boiler 110 and second boiler feed line 82 which enters second boiler 90.

Second boiler exit line 92 and first boiler exit line 94 are combined into process steam line 96 which conveys steam 57 to the process.

Sample line 52, draws off a sample of boiler feedwater from boiler feed line 87 by an "on-off" activation of sample valve 27. The sample is conveyed through sample line 52 through fluorometer feed valve 54 into fluorometer 50. The fluorescent signal of unreacted or 'residual' Oxygen Scavenger is detected. Each Oxygen Scavenger requires the fluorometer to have its excitation and emission wavelengths set to match the Oxygen Scavenger. When the Oxygen Scavenger is Gallic Acid, the residual Oxygen Scavenger is detected by setting fluorometer 50 at about 300 nm excitation and about 370 nm emission. When the Oxygen Scavenger is Hydroquinone, the residual Oxygen Scavenger is detected by setting fluorometer 50 at about 290 nm excitation and about 325 nm emission. When the Oxygen Scavenger is propyl gallate the residual Oxygen Scavenger is detected by setting fluorometer 50 at about 320 nm excitation and about 390 nm emission. When the Oxygen Scavenger is 3,4-dihydroxybenzhydrazide the residual Oxygen Scavenger is detected by setting fluorometer 50 at about 320 nm excitation and about 400 nm emission. When the Oxygen Scavenger is 2-hydroxybenzhydrazide the residual Oxygen Scavenger is detected by setting fluorometer 50 at about 320 nm excitation and about 430 nm emission. When the Oxygen Scavenger is 4-hydroxybenzhydrazide the residual Oxygen Scavenger is detected by setting fluorometer 50 at about 290 nm excitation and about 350 nm emission. When the Oxygen Scavenger is salicylal carbohydrazone the residual Oxygen Scavenger is detected by setting fluorometer 50 at about 330 nm excitation and about 470 nm emission.

With respect to fluorometric detection of Gallic Acid; Gallic Acid has a detectable fluorescent signal at neutral and basic pH. Gallic Acid is also fluorescent at acidic pH, however, at the lower pH there is a limitation on the solubility of Gallic Acid, therefore, the fluorescent signal of Gallic Acid at acidic pH is difficult to quantify. In practice, boiler water is always either at a neutral or basic pH, therefore, the solubility limits of Gallic Acid at acid pH and the effect upon Gallic Acid's fluorescent signal is not an impediment to the practice of the instant claimed invention.

In the first aspect of the instant claimed invention, sample line 52, draws off a sample of boiler feedwater from boiler feed line 87 by an "on-off" activation of sample valve 27. The sample is conveyed through sample line 52 through fluorometer feed valve 54 into fluorometer 50. Fluorometer 50 detects the fluorescent signal of residual Oxygen Scavenger. The fluorometer is pre-programmed to convert the fluorescent signal of residual Oxygen Scavenger into a concentration value for residual Oxygen Scavenger using a conversion graph.

Figure 6:
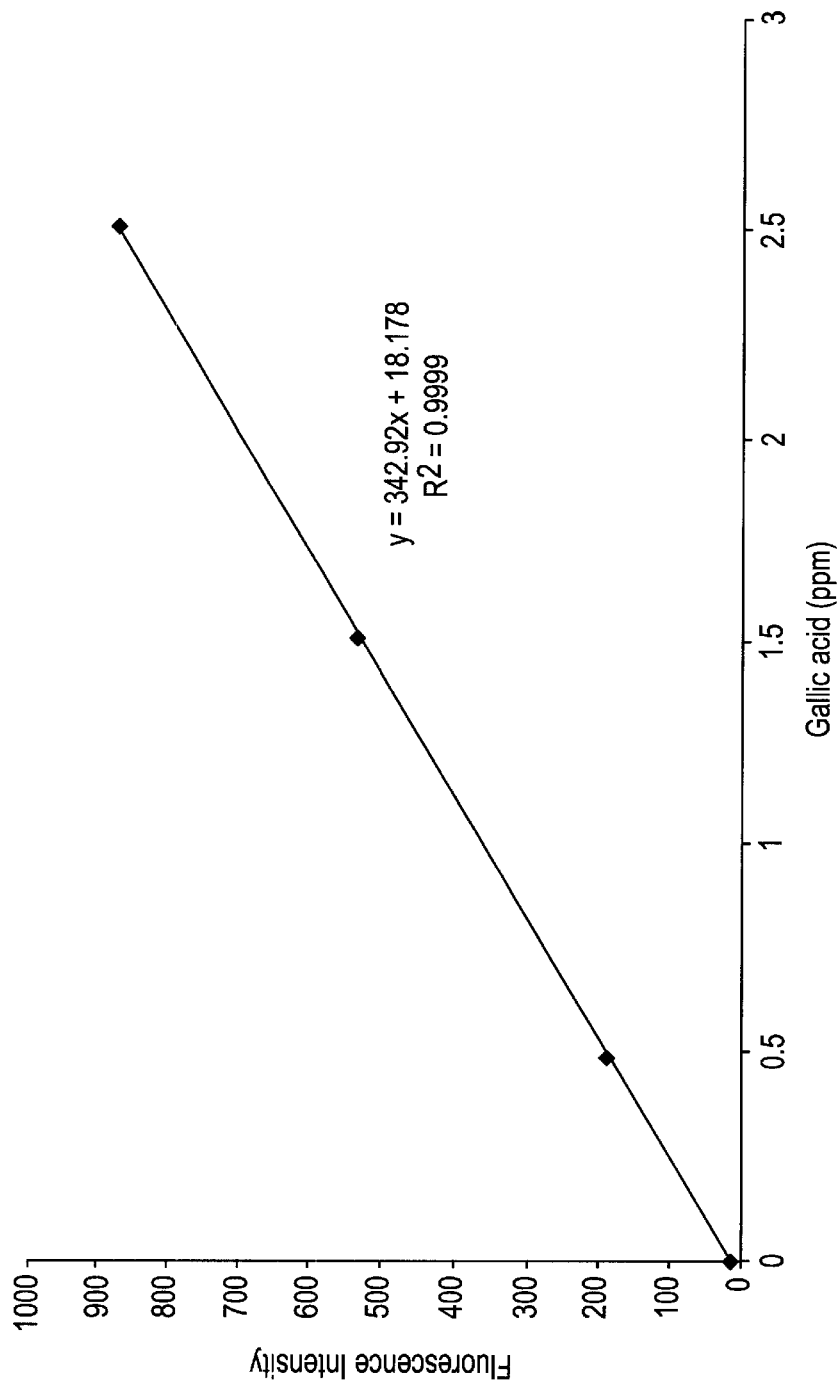
FIG. 6 shows a plot of fluorescent signal (dimensionless number) of Gallic Acid vs. the concentration, in ppm, of Gallic Acid using a Hitachi Xenon-Pulse F4500 fluorometer.
Figure 7:
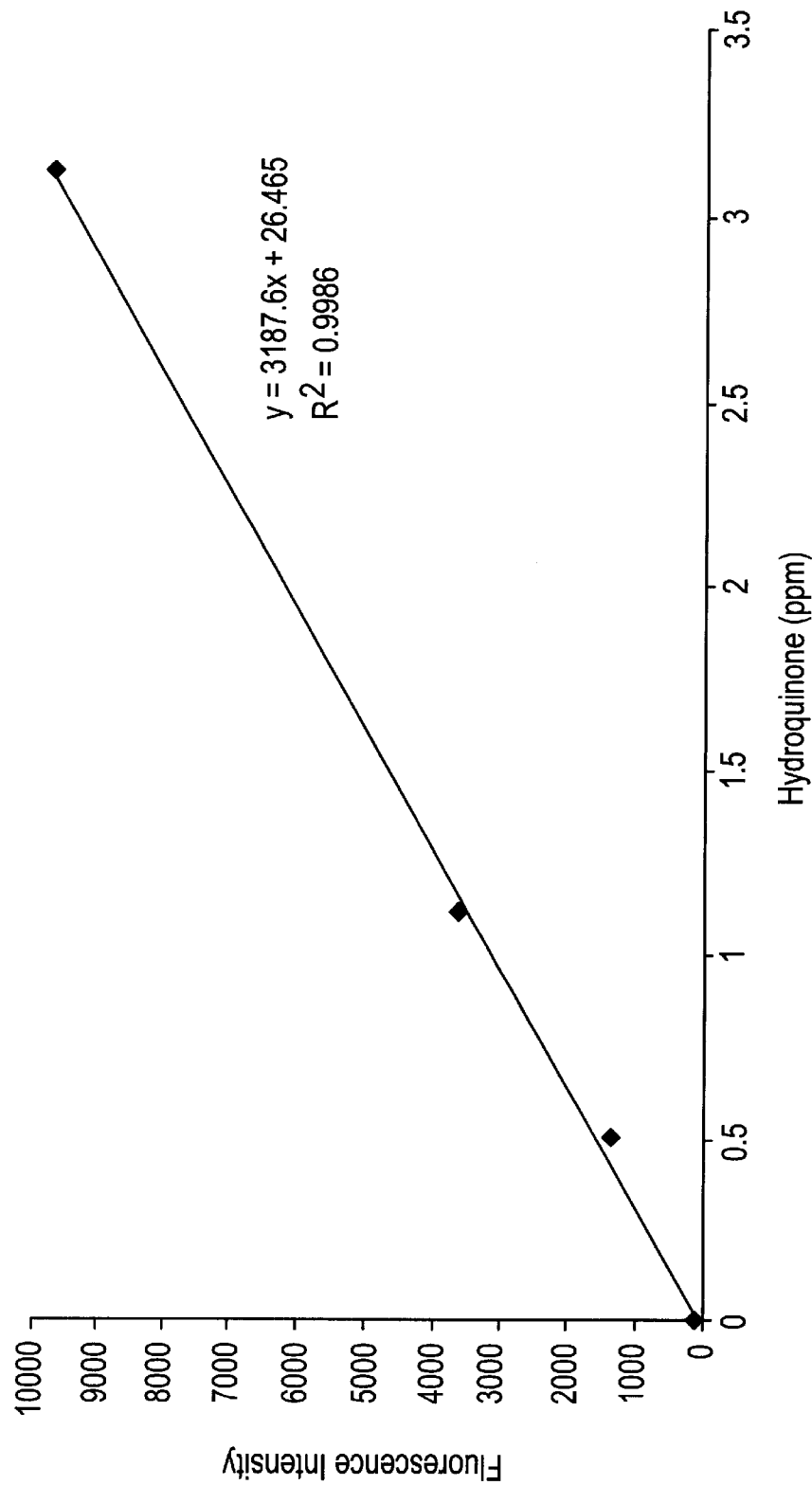
FIG. 7 shows a plot of fluorescent signal (dimensionless number) of Hydroquinone vs. the concentration, in ppm of Hydroquinone using a Hitachi Xenon-Pulse F4500 fluorometer.

The conversion graph for Gallic Acid is shown in FIG. 6, which shows the amount of detected fluorescent signal, a dimensionless number, present plotted against the concentration of Gallic Acid. The conversion graph for Hydroquinone is shown in FIG. 7, which shows the amount of detected fluorescent signal, a dimensionless number, present plotted against the concentration of Hydroquinone. Both FIG. 6 and FIG. 7 were created using a Hitachi F4500 Xenon-Pulse Fluorometer.

Figures showing the relationship between concentration of Gallic Acid or Hydroquinone to Fluorescence Intensity were generated on a Hitachi F4500 Xenon-Pulse Fluorometer. Fluorescence Intensity is an arbitrary unitless designation defined by Hitachi, to express the amount of emitted light that reaches a photomultiplier tube detector and/or the amount of energy applied to the detector to generate a fluorescence signal. Settings on the fluorometer can be modified to amplify or reduce the amount of emitted light and/or energy to the detector. Slit width is the most common way to adjust the amount of emitted light reaching the detector. The wider the slit width, the more light is exposed to the sample and/or the detector. Slit widths can be changed on both the excitation and emission.

The amount of energy applied to the detector can also affect the Fluorescence Intensity. This approach is similar to applying a gain to the fluorescent signal. The Hitachi F4500 has three voltage settings on the detector. A 700 V setting is the instrument default.

The fluorometer settings used for the Gallic acid linear plot are slits (excitation/emission): 5.0 nm/5.0 nm and 700 V on the detector. The fluorometer settings used for the Hydroquinone linear plot are slits (ex/em): 10.0 nm/10.0 nm and 700 V on the detector.

After the concentration value of residual Oxygen Scavenger is determined, it is compared to a setpoint value for what the residual Oxygen Scavenger concentration is supposed to be for the particular Boiler System. This setpoint value is determined for each Boiler System and is based on the value for residual Oxygen Scavenger that is observed when the Boiler System is running optimally.

Fluorometers useful in the method of the instant claimed invention are available from Nalco.

If there is more residual Oxygen Scavenger present then is wanted, the output signal 51 from fluorometer 50 is used to turn off or decrease the flow rate of Fresh Oxygen Scavenger Product feedpump 70. In contrast, if there is less residual Oxygen Scavenger present then is wanted, the output signal 51 from fluorometer 50 is used to turn on or increase the flow rate of Fresh Oxygen Scavenger Product feedpump 70.

By using the equipment set up in FIG. 1, it is possible to automatically control the amount of Fresh Oxygen Scavenger Product (oxygen scavenger) present in the water going into the boilers. This automatic control provides for better control of having the optimal amount of oxygen scavenger present in a Boiler System as there is less lag time between detecting a system upset and adjusting the flowrate of Fresh Oxygen Scavenger Product accordingly.

The second aspect of the method of the instant claimed invention is a method of enhancing the fluorescent signal of a fluorescent oxygen scavenger compound comprising:

a) providing a stream comprising a fluorescent oxygen scavenger compound selected from the group consisting of compounds with two or three adjacent hydroxyl groups on an aromatic ring;

b) providing one fluorometer;

c) adding borate to said stream; and d) using said fluorometer to detect the fluorescent signal of said fluorescent oxygen scavenger in said stream.

The second aspect of the method of the instant claimed invention is based on the fact that it has been found that the fluorescent signal of certain aromatic oxygen scavengers can be enhanced by the addition of borate. These fluorescent oxygen scavenger compounds are selected from the group consisting of compounds with two or three adjacent hydroxyl groups on an aromatic ring. For purposes of this patent application, aromatic rings are selected from the group consisting of benzene, naphthalene, anthracene, phenanthrene and phenalene. Suitable compounds with two or three adjacent hydroxyl groups on an aromatic ring include, but are not limited to Gallic Acid, 3,4,5-trihydroxybenzoic acid, propyl ester, 2,3-dihydroxynaphthalene, 3,4-dihydroxybenzoic acid and 3,4-dihydroxybenzhydrazide. The preferred compound is Gallic Acid.

The enhancement of fluorescent signal is not observed for all aromatic oxygen scavengers, for example, it has been found that the fluorescent signal of Hydroquinone is not enhanced by the addition of borate.

The amount of typically observed enhancement is pH dependent as is shown in this table:

| Substance | pH | Magnitude of fluorescent signal enhancement |
| --- | --- | --- |
| 3,4,5-trihydroxybenzoic acid | 9.2 | 15 times |
| 3,4,5-trihydroxybenzoic acid | 11.0 | 7 times |
| 3,4,5-trihydroxybenzoic acid, propyl ester | 9.2 | 1.3 times |
| 3,4,5-trihydroxybenzoic acid, propyl ester | 11.0 | 6 times |
| 2,3-dihydroxynaphthalene | 9.2 | 8 times |
| 3,4-dihydroxybenzoic acid | 9.2 | 24 times |
| 3,4-dihydroxybenzoic acid | 11.0 | 14 times |
| 3,4-dihydroxybenzhydrazide | 9.2 | 1.4 times |

Figure 2:
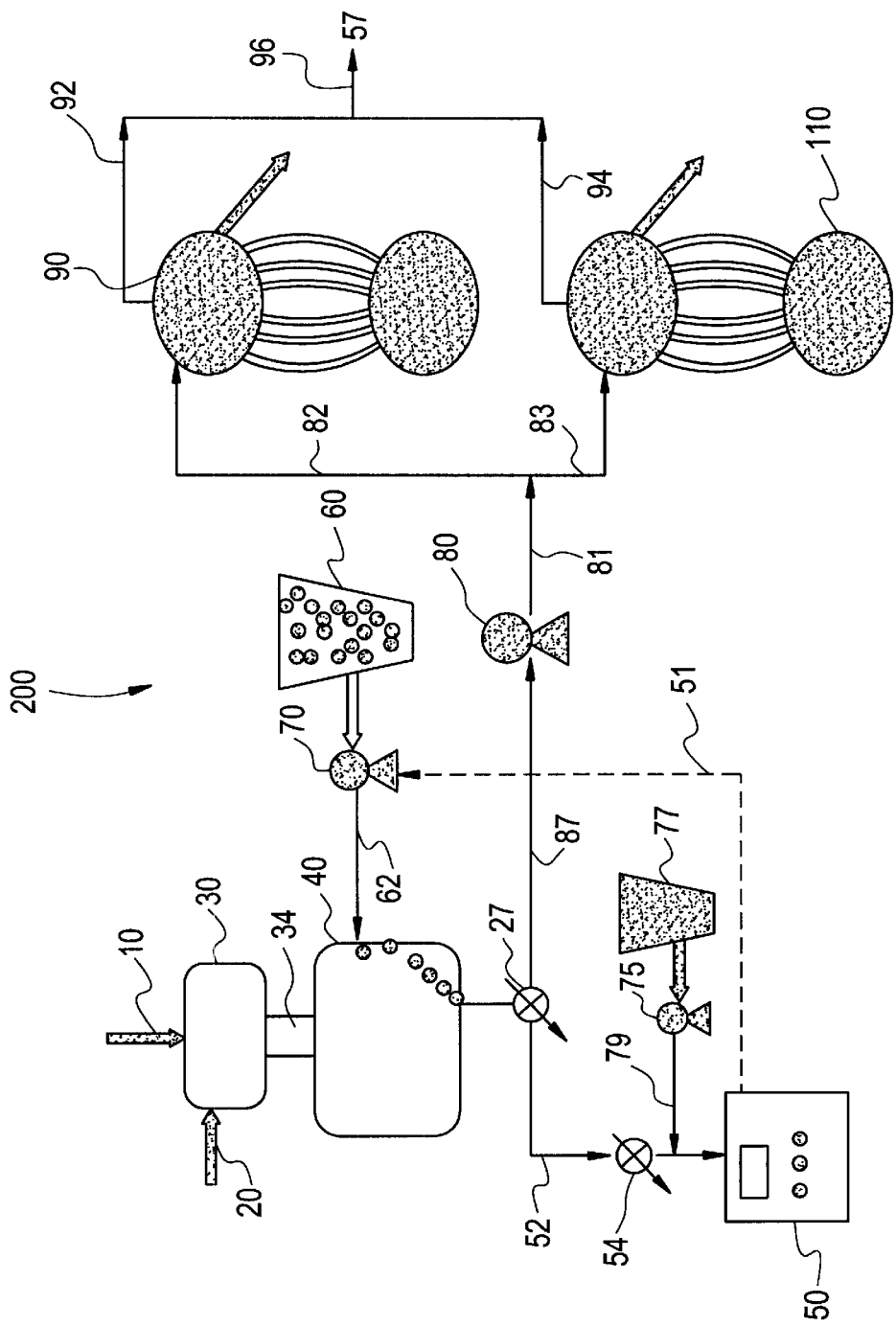
FIG. 2 shows the same Boiler System as FIG. 1, with the addition of a source of borate and a feedpump for borate so that borate can be added to the sampling stream that is being sent to the fluorometer.

FIG. 2 shows second Boiler System 200, which is configured the same as first Boiler System 100, with the addition of borate source tank 77, borate feedpump 75 and borate feed line 79. In second Boiler System 200, borate from borate source tank 77 is pumped through borate feedpump 75 and enters sample line 52. The borate source is a sodium tetraborate buffer solution. The concentration of the sodium tetraborate buffer solution is from about 0.05M to about 0.2M, preferably about 0.2M. The buffer solution is added to sample line 52. The ratio of buffer solution to volume of sample stream (buffer:sample ratio) is from about 1:3 to about 1:10, preferably from about 1:5 to about 1:10 and most preferably from about 1:7 to about 1:10.

The configuration shown in FIGS. 2–5, shows borate being added only to the sample stream entering the fluorometer. Although, this is the preferred method of adding borate, it would also be possible to add the borate along with the Fresh Oxygen Scavenger Product.

Because the enhancement of the fluorescent signal makes it easier to detect the presence of residual Oxygen Scavenger, the preferred way of conducting the method of the instant claimed invention is by having the fluorescent signal of the residual Oxygen Scavenger be enhanced by adding borate to the sample stream.

The third aspect of the instant claimed invention is a method to control the addition of Ultimate Oxygen Scavenger to a Boiler System comprising:

a) providing a Boiler System;

b) providing two fluorometers and a controller;

c) using the first of said two fluorometers to detect the fluorescent signal of residual Ultimate Oxygen Scavenger in the boiler feedwater;

d) using the second of said two fluorometers to detect the fluorescent signal of oxidized Ultimate Oxygen Scavenger in the boiler feedwater;

e) calculating a ratio of said residual Ultimate Oxygen Scavenger to said oxidized Ultimate Oxygen Scavenger in the boiler feedwater; and f) using said controller to control the amount of Fresh Ultimate Oxygen Scavenger Product added to said Boiler System based on comparing the calculated ratio of said residual Ultimate Oxygen Scavenger to said oxidized Ultimate Oxygen Scavenger in said boiler feedwater to an optimal setpoint ratio of said residual Ultimate Oxygen Scavenger to said oxidized Ultimate Oxygen Scavenger in said boiler feedwater.

Figure 3:
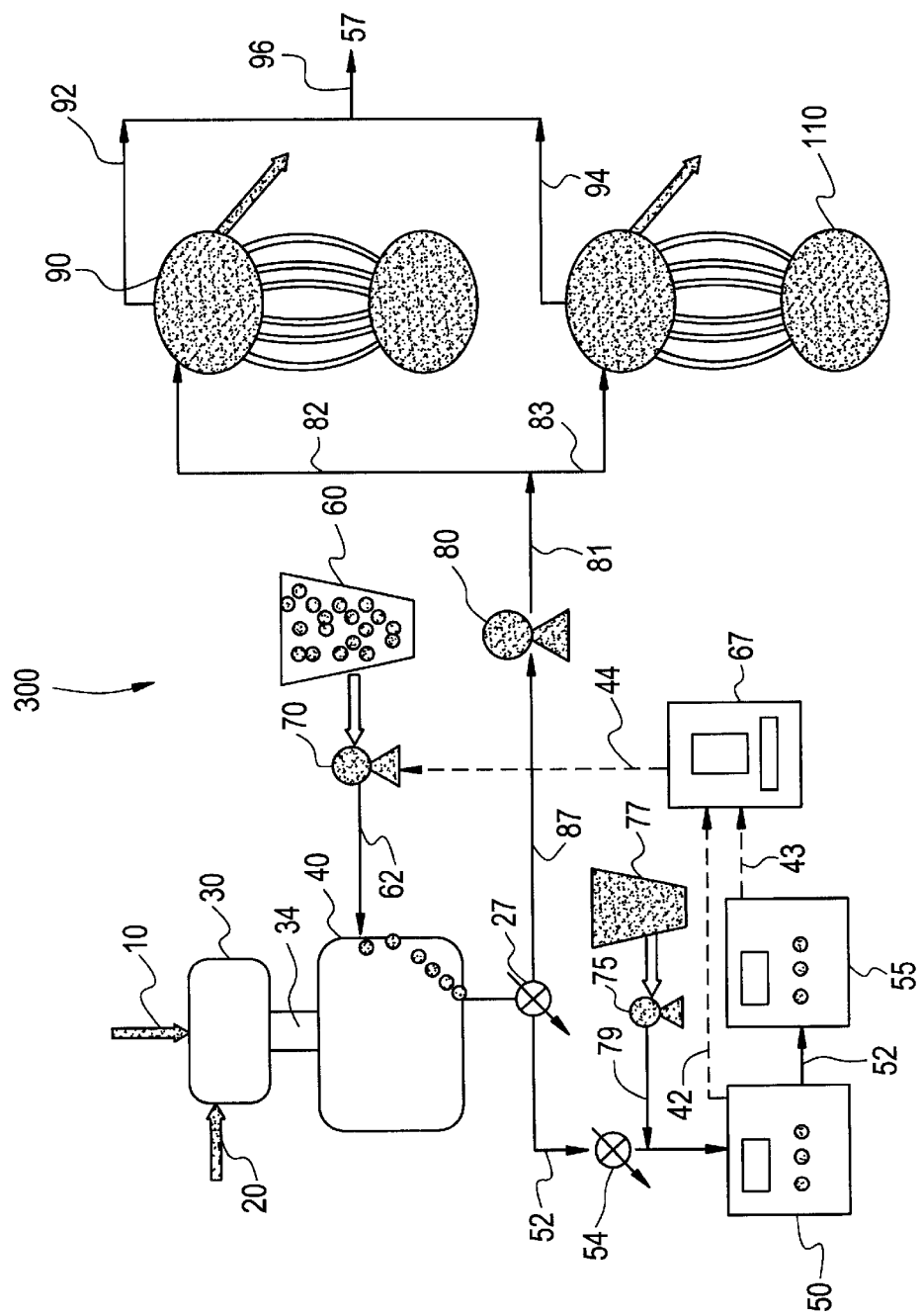
FIG. 3 shows the same Boiler System as FIG. 2, with the addition of a second fluorometer so that residual Ultimate Oxygen Scavenger in its residual unreacted state and Ultimate Oxygen Scavenger in its oxidized ("reacted") state can be detected. The signals of both fluorometers are then used to control the feed rate of Fresh Ultimate Oxygen Scavenger Product to the Boiler System.

The third aspect of the instant claimed invention is illustrated in FIG. 3. In FIG. 3, Third Boiler System 300 is set up the same as Second Boiler System 200, with the addition of a second fluorometer 55 and controller 67. Fresh Oxygen Scavenger Product in this Figure must be Fresh Ultimate Oxygen Scavenger Product. Sample line 52 enters first fluorometer 50, where the fluorescent signal of residual Ultimate Oxygen Scavenger is detected and then sample line 52 continues on into second fluorometer 55. Second fluorometer 55 is set up to detect the fluorescent signal of the oxidized Ultimate Oxygen Scavenger.

Suitable Ultimate Oxygen Scavengers must have a detectable fluorescent signal both in their reduced and in their oxidized form. Ultimate Oxygen Scavengers, include, but are not limited to, Gallic Acid. When the Ultimate Oxygen Scavenger is Gallic Acid, the fluorescent signal of the oxidized Ultimate Oxygen Scavenger (5-hydroxy, 3,4-dioxo, 1,5-cyclohexanediene-1-carboxylic acid) is detected by having fluorometer 55 configured at about 360 nm excitation and about 440 nm emission.

First fluorometer output signal 42 and second fluorometer output signal 43 enter controller 67. Controller 67 calculates the ratio of residual Ultimate Oxygen Scavenger to oxidized Ultimate Oxygen Scavenger and compares it to the preprogrammed setpoint ratio of residual Ultimate Oxygen Scavenger to oxidized Ultimate Oxygen Scavenger. After the comparison is complete, controller 67 sends a signal 44 to Fresh Ultimate Oxygen Scavenger Product feedpump 70 to either turn on the pump or increase the flow rate of the pump or turn off the pump or decrease the flow rate of the pump, depending upon how far from optimal setpoint the desired ratio is calculated to be.

Figure 4:
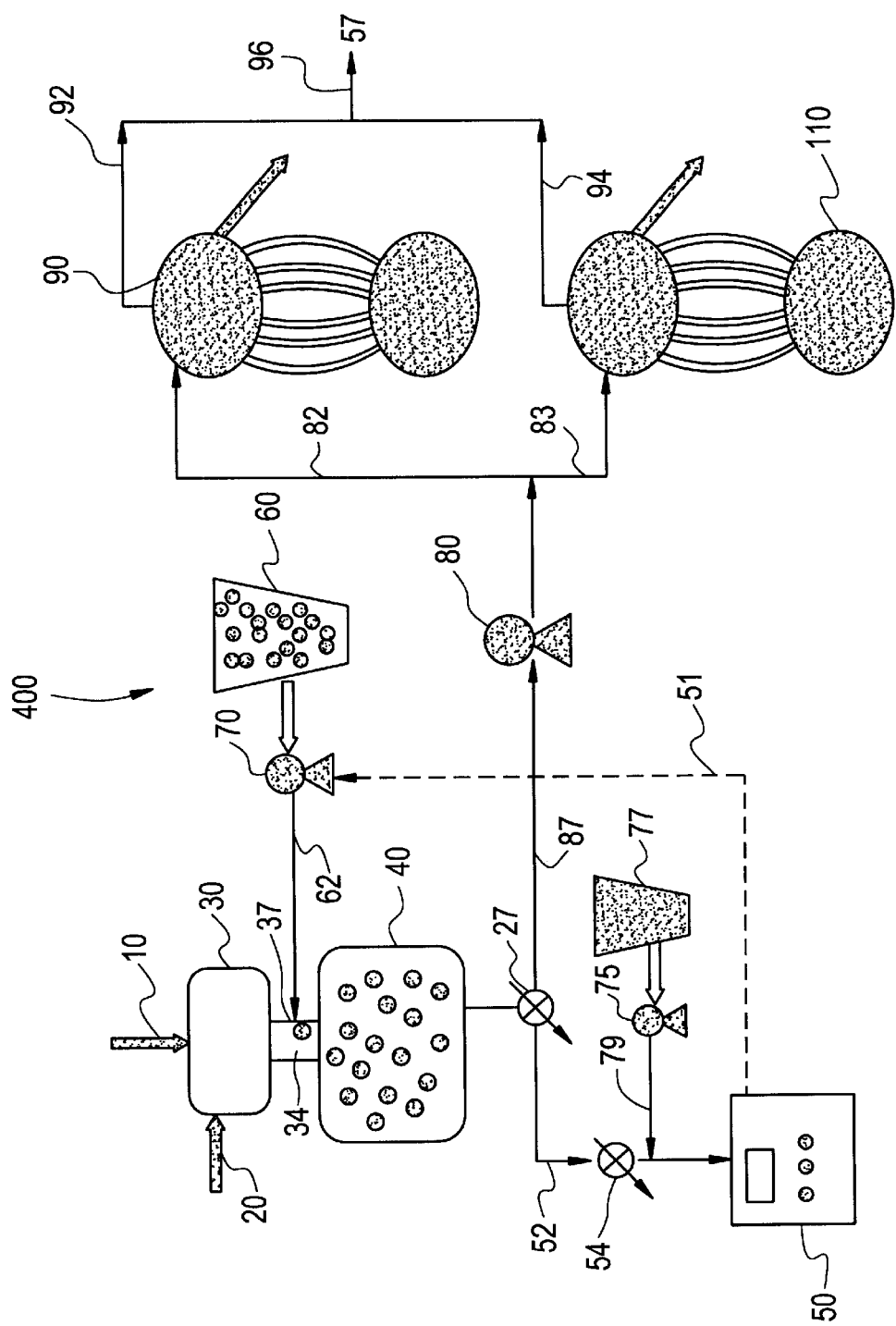
FIG. 4 shows the same Boiler System as FIG. 2, except for the fact that the point of addition of Fresh Oxygen Scavenger Product to the Boiler System has been changed to the deaerator dropleg.

FIG. 4 illustrates Fourth Boiler System 400 which shows the same Boiler System as FIG. 2 with a change being made in the location of the addition of Fresh Oxygen Scavenger Product. The change involves moving the addition point of Fresh Oxygen Scavenger Product from deaerator storage section 40 to the deaerator drop leg 34 at addition point 37. Addition point 37 is optimally selected in this way to enhance the mixing, and thus the complete distribution, of Fresh Oxygen Scavenger Product 60 in deaerator storage section 40. Further optimization involves the use of an injection quill 38 (not shown) that extends beyond the internal surface of the deaerator. The use of an injection quill 38, rather than coupling device 41 is recommended to reduce 'channeling' of the Fresh Oxygen Scavenger Product in deaerator storage section 40. Injection quills are known in the art of chemical engineering and can be obtained from any chemical process equipment company.

Figure 5:
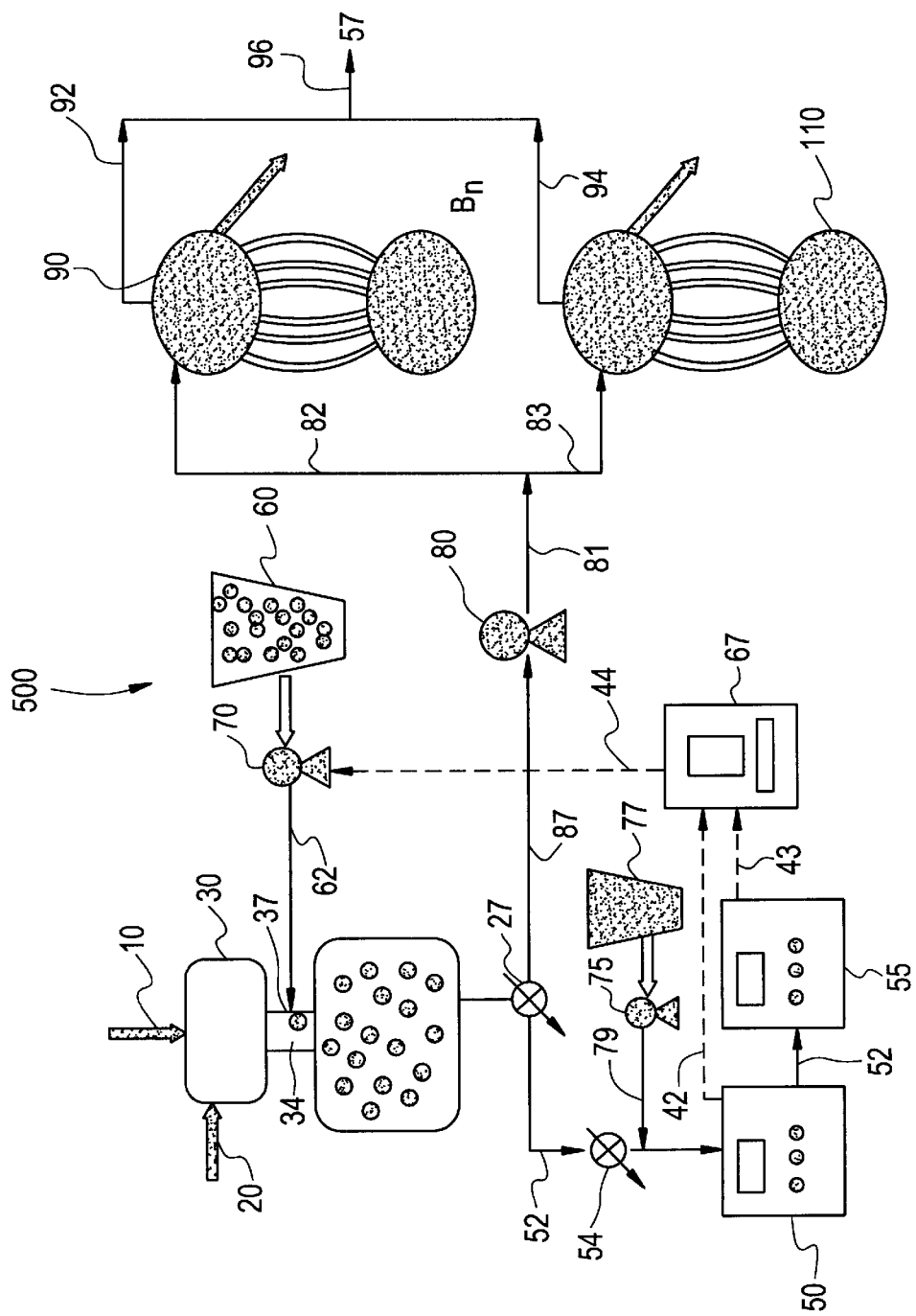
FIG. 5 shows the same Boiler System as FIG. 3, except for the fact that the point of addition of Fresh Ultimate Oxygen Scavenger Product to the Boiler System has been changed to be in the neck of the deaerator.

FIG. 5 shows Fifth Boiler System 500 which is the same as Third Boiler System 300 with the addition that the point of addition for Fresh Ultimate Oxygen Scavenger Product has been moved from deaerator storage section 40 to the deaerator drop leg 34 at injection point 37.

In conducting the method of the instant claimed invention it has been found possible to more accurately control the addition of Fresh Oxygen Scavenger Product to a Boiler System. It has been found highly beneficial to the operation of a Boiler System when the amount of oxygen scavenger present is being automatically controlled to a predetermined setpoint.

The following examples are presented to describe preferred embodiments and utilities of the invention and are not meant to limit the invention unless otherwise stated in the claims appended hereto.

EXAMPLES

In all of these examples the following experimental setup is used: Fresh Oxygen Scavenger Product is fed to a Boiler System at a Mid-Western paper mill. The Oxygen Scavenger Product is Gallic Acid Product 1, which has the formula:

| | |
|---|---|
| Deionized water | 89.93% |
| 50% NaOH | 4.54% |
| Gallic Acid monohydrate | 5.53% |

The Boiler System has 2 boilers that operate at 100 psig and 20–25 cycles. Gallic Acid is fed directly into the side of the deaerator storage section through a coupling device. Water from the deaerator is taken to a high pressure boiler feedpump that feeds the 2 operating boilers. Steam generated from the system is used for paper manufacture and processing.

Example 1
Gallic Acid Residual Fluorometric Monitoring in Boiler Feed Line

The Gallic Acid residual is monitored in the deaerator storage section using an online fluorometer (TRASAR® 200 System Part No. 081-TSR201.88 available from Nalco). The lamp and filters on the fluorometer are designed to specifically measure Gallic Acid in the reduced (unreacted) form (TRASAR® 1 lamp available from Nalco Part No. 741-Y00182.88 and 300FS25 excitation and 370FS25 emission filters available from Andover). The gain on the fluorescent output is maximized to improve sensitivity. The sample lag time from the storage section to the fluorometer is minimized.

The product set point (in either ppm Product or ppb Oxygen Scavenger Actives) and control range (in either ppm Product or ppb Oxygen Scavenger Actives) is used to control an on/off signal to the LMI Fresh Oxygen Scavenger Product feedpump. The product set point for this examples is 12 ppm Product or 600 ppb Gallic Acid. The control range is ±2 ppm product or 100 ppb Gallic Acid. See FIG. 1 for a schematic of the boiler system.

Initial control of the residual Gallic Acid is adequate, but less than optimal, with 1 standard deviation of the data at over 50% of the setpoint. Spikes in the dissolved oxygen concentration above 500 ppb are recorded using an online dissolved oxygen meter.

Example 2
Borate Enhanced Gallic Acid Residual Fluorometric Monitoring in Boiler Feed Line This example was conducted using the equipment set-up of FIG. 2, with the operating parameters as described in Example 1.

Sodium tetraborate buffer (0.2 M) is added to the sample stream at a 1:7 buffer:sample ratio to stabilize the pH and enhance the fluorescent signal 15 fold. The sensitivity of the fluorometer for the reduced Gallic Acid signal increases such that the gain on the fluorometer must be turned down. Control of the Gallic Acid residual improves with 1 standard deviation of the data at 25% of the setpoint. Spikes in the dissolved oxygen concentration above 200 ppb are still observed.

Example 3
Borate Enhanced Gallic Acid Residual and Oxidized Oxygen Scavenger Fluorometric Monitoring in Boiler Feed Line This example was conducted using the equipment set-up of FIG. 3, with the operating parameters as described in Example 1 and the Borate Enhancement as described in Example 2. This is an example of the use of Ultimate Oxygen Scavenger.

A second fluorometer is put online for the measurement of the oxidized Ultimate Oxygen Scavenger fluorometric signal (TRASAR® 350 configuration for oxidized Gallic Acid uses TRASAR® 2 lamp available from Nalco, Part No. 741-Y00194.88 and 360FS10 excitation and 450FS10 emission filters available from Andover). Signals from both fluorometers are sent to a controller. The controller calculates ratio of residual Ultimate Oxygen Scavenger to oxidized Ultimate Oxygen Scavenger and compares that calculated ratio to a setpoint.

When the ratio does not match the setpoint, the controller sends a signal to the Fresh Ultimate Oxygen Scavenger Product feedpump to adjust the flowrate of Fresh Ultimate Oxygen Scavenger Product into the Boiler System. Control improves with one standard deviation of the data at 15% of the Gallic Acid residual setpoint.

Example 4
Borate Enhanced Gallic Acid Residual Fluorometric Monitoring in Boiler Feed Line with Optimal Feed Configuration This example was conducted using the equipment set-up of FIG. 4, with the operating parameters as described in Example 1 and the Borate Enhancement as described in Example 2.

The product feedpoint and deaerator operation are examined for additional ways to improve control of the residual Gallic Acid. Operations at the site confirm that the Gallic Acid injection into the deaerator storage section is done without an injection quill that would extend beyond the internal surface of the deaerator. The intake to the boiler feedpump is off center in the direction of the Gallic Acid feedpoint. Average concentrations of Gallic Acid at the intake are over twice the concentrations found at the sampling point. Channeling of the Gallic Acid in the deaerator is expected.

It is recommended that operations at the site change the Gallic Acid product feed point to the deaerator dropleg 34 between the dome and storage section to improve mixing of the Gallic Acid in the storage section. See FIG. 4 for the optimal feed configuration.

Monitoring and control are resumed using the same set point and control range used previously. Control of the residual Gallic Acid dramatically improves with 1 standard deviation of the data at 5% of the setpoint.

Example 5
Measurement of Ultimate Oxygen Scavenger

This example was conducted using the equipment set-up of FIG. 5, with the operating parameters as described in Example 4 and the Borate Enhancement as described in Example 2. This is an Example of the use of Ultimate Oxygen Scavenger product.

Further control of the residual Gallic Acid setpoint is achieved at the optimal feed configuration with the use of 2 fluorometers measuring the residual Gallic Acid and oxidized Gallic Acid. Signals are sent from both fluorometers to a controller. The controller calculates a ratio of residual Ultimate Oxygen Scavenger to oxidized Ultimate Oxygen Scavenger and compares that calculated ratio to a setpoint. When the ratio does not match the setpoint, the controller sends a signal to the Ultimate Oxygen Scavenger Product feedpump to adjust the flowrate of Ultimate Oxygen Scavenger Product into the Boiler System.

Under this configuration, control of the Gallic Acid residual improves yet again with 1 standard deviation of the data a 2% of the setpoint.

Changes can be made in the composition, operation and arrangement of the method of the present invention described herein without departing from the concept and scope of the invention as defined in the following claims:

What is claimed is:

1. A method to control the addition of fresh oxygen scavenger product to a boiler system comprising:
   a) providing a boiler system;
   b) providing one fluorometer;
   c) using said one fluorometer to detect the fluorescent signal of residual oxygen scavenger present in the boiler feedwater;
   d) converting the fluorescent signal of said residual oxygen scavenger to the amount of said residual oxygen scavenger present in the boiler feedwater; and
   e) controlling the amount of fresh oxygen scavenger product being added to said boiler system based on the amount of residual oxygen scavenger fluorometrically detected in said boiler wherein said fresh oxygen scavenger product comprises a compound selected from the group consisting of gallic acid, hydroquinone, propyl gallate, 3,4-dihydroxybenzhydrazide, 2-hydroxybenzhydride, 4-hydroxybenzhydrazide and salicylal carbohydrazone feedwater.

2. A method to control the addition of fresh ultimate oxygen scavenger product to a boiler system comprising:
   a) providing a boiler system;
   b) providing two fluorometers and a controller;
   c) using the first of said two fluorometers to detect the fluorescent signal of residual ultimate oxygen scavenger in the boiler feedwater;
   d) using the second of said two fluorometers to detect the fluorescent signal of oxidized ultimate oxygen scavenger in the boiler feedwater;
   e) calculating a ratio of said residual ultimate oxygen scavenger to said oxidized ultimate oxygen scavenger in the boiler feedwater; and
   f) using said controller to control the amount of fresh ultimate oxygen scavenger product added to said boiler system based on comparing the calculated ratio of said residual ultimate oxygen scavenger to said oxidized ultimate oxygen scavenger in said boiler feedwater to an optimal setpoint ratio of said residual ultimate oxygen scavenger to said oxidized ultimate oxygen scavenger in said boiler feedwater.

3. The method of claim 2 where said fresh ultimate oxygen scavenger product comprises gallic acid.

4. The method of claim 1 in which said fresh oxygen scavenger product comprises gallic acid.

* * * * *